US005674895A

United States Patent [19]
Guittard et al.

[11] Patent Number: 5,674,895
[45] Date of Patent: Oct. 7, 1997

[54] DOSAGE FORM COMPRISING OXYBUTYNIN

[75] Inventors: George V. Guittard, Cupertino; Francisco Jao; Susan M. Marks, both of San Jose; David J. Kidney, Sunnyvale; Fernando Gumucio, Santa Clara, all of Calif.

[73] Assignee: Alza Corporation, Palo Alto, Calif.

[21] Appl. No.: 445,849

[22] Filed: May 22, 1995

[51] Int. Cl.$^6$ .................... A01N 37/44; A61K 31/24
[52] U.S. Cl. .................. 514/534; 424/464; 424/468; 424/474; 424/475; 424/479; 424/480; 424/484; 424/486; 424/488
[58] Field of Search .................. 424/464, 467, 424/468, 474, 475, 479, 480, 484, 486, 488; 514/579, 646, 663, 727, 729, 730, 534

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,063,064 | 12/1977 | Saunders et al. | 219/121 |
| 4,088,864 | 5/1978 | Theeuwes et al. | 219/121 |
| 4,111,202 | 9/1978 | Theeuwes et al. | 128/260 |
| 4,285,987 | 8/1981 | Ayer et al. | 428/3 |
| 4,327,725 | 5/1982 | Cortese et al. | 128/260 |
| 4,612,008 | 9/1986 | Wong et al. | 604/892 |
| 4,783,337 | 11/1988 | Wong et al. | 424/468 |
| 4,800,098 | 1/1989 | Ayer et al. | 128/260 |
| 4,816,263 | 3/1989 | Ayer et al. | 424/468 |
| 4,824,675 | 4/1989 | Wong et al. | 424/438 |
| 4,863,456 | 9/1989 | Stephens et al. | 604/892.1 |
| 4,902,514 | 2/1990 | Barclay et al. | 424/473 |
| 5,399,359 | 3/1995 | Baichwal | 424/464 |

OTHER PUBLICATIONS

"General principles for designing with plastics" by P. Grafton, 1969–1970 Modern Plastics Encyclopedia, vol. 46, pp. 62–70.

"Preparation of Compressed Tablet Granulations by the Air–Suspension Technique II" by Dale E. Wurster, J. of Amerc. Phar. Association vol. 49 No. 2, pp. 82–84, Feb. 1960.

"Air–Suspension Technique of Coating Drug Particles" by Dale E. Wurster, J. Am Phar. Assoc. Sci. Ed., vol. 48, pp. 451454, Aug. 1959.

Pharmaceutical Science, By Remington, 14th Ed., pp. 1626–1979, (1970).

Chemical Abstracts, vol. 120, No. 18, May 2, 1994, Abstract No. 227011.

Chemical Abstracts, vol. 120, No. 14, Apr. 4, 1994, Abstract No. 173499.

*Primary Examiner*—James J. Seidleck
*Assistant Examiner*—Michael A. Williamson
*Attorney, Agent, or Firm*—Paul L. Sabatine; Mary Ann Dillahunty; Michael J. Rafa

[57] ABSTRACT

A composition comprising oxybutynin and a device comprising oxybutynin are disclosed for oxybutynin therapy.

7 Claims, No Drawings

5,674,895

DOSAGE FORM COMPRISING OXYBUTYNIN

This invention pertains to a novel dosage form comprising oxybutynin. The invention relates also to a therapeutic composition comprising oxybutynin, and the invention concerns additionally a method for administering oxybutynin to a patient in need of oxybutynin.

BACKGROUND OF THE INVENTION

Many people are affected by urinary incontinence. Incontinence is particularly common in the elderly, urinary incontinence is present in approximately fifty percent of nursing home patients, and urinary incontinence is a well-known urologic problem in women. It will affect nearly all women in some form during their lifetime, and it is of significant social concern to all humans who experience it.

Urinary incontinence arises from the anatomy and the physiology of the urinary tract, which is composed of a bladder and a sphincter. Anatomically, the bladder consists of the bladder musculature, also known as detrusor, and the trigone. The sphincter includes the bladder neck and the propimal urethra. The detrusor muscle is innervated by the pelvic nerve through the parasympathetic nervous system, and the bladder neck and proximal urethra are innervated by the sympathetic nervous system.

The major functions of the bladder are the storage and expulsion of urine. The bladder is responsible for accommodating increasing volumes of urine at low pressures. Normally, the bladder remains closed during bladder filling, and continence is maintained as long as the bladder neck and urethral pressure exceeds intravesical pressure. Voluntary voiding occurs when intravesical pressure exceeds bladder neck and urethral pressure, and involuntary voiding occurs when the intravesical pressure exceeds the bladder neck and urethral pressure.

Involuntary incontinence also known as urge incontinence occurs with a loss of large a volume of urine accompanied by symptoms of urgency, frequency and nocturia caused by an unstable bladder or detrusor instability. The patient may lose urine with a change in position or with auditory stimulation. The loss of small volumes of urine usually occurs because of bladder overdistention by a large amount of residual urine referred to as overflow incontinence.

The management of incontinence consists in administering a smooth-muscle relaxant such as oxybutynin, which acts directly on the smooth-muscle at the site distal to the cholinergic receptor. The usual dose in the pharmacologic management is repeated doses from two-to-four times a day for oxybutynin. This is difficult to achieve as it requires rigid compliance and it is cost ineffective. Also, oxybutynin is adversely affected by light, and it needs protection from air which properties do not lend the drug to formulation into a dosage form that can administer oxybutynin at a controlled and known rate per unit time to produce the intended therapy.

In the light of the above presentation, it will be appreciated by those versed in the medical and in the pharmaceutical dispensing arts to which this invention pertains, that a pressing need exists for a dosage form that can deliver the valuable drug oxybutynin in a rate-controlled dose to a patient in clinical need of incontinence management. The pressing need exists also for an oral dosage form and for a method of therapy that can deliver oxybutynin at a controlled rate in a substantially constant dose per unit time for its beneficial therapeutic effect. The need exists further for a dosage form that can deliver oxybutynin substantially protected from light to insure a complete dose of oxybutynin is administered to the patient and still remain substantially independent of the changing environment of the gastrointestinal tract. The need exists additionally for a dosage form that can deliver a therapeutic dose of oxybutynin for its intended effect and also lessen the side-effects that can accompany the drug. It will be appreciated further by those skilled in the dispensing art, that if such a novel and unique dosage form and method are made available that can administer oxybutynin in a rate-controlled dose over time, and simultaneously provide oxybutynin for lessening the incident of incontinence, the dosage form and its accompanying method would represent an advancement and a valuable contribution to the medical arts.

OBJECTS OF THE INVENTION

Accordingly, in view of the above presentation, it is an immediate object of this invention to provide a dosage form for delivering oxybutynin in a rate-controlled dose, and which dosage form substantially overcomes the deficiencies and omissions associated with the prior art.

Another object of the present invention is to provide a dosage form for orally administering oxybutynin in a rate-controlled dose for the nonsurgical treatment of incontinence in a human afflicted with incontinence.

Another object of the invention is to provide a pharmacologic composition comprising oxybutynin indicated for the pharmacologic management of incontinence.

Another object of the present invention is to provide a pharmacologic composition comprising oxybutynin, its racemate, its R-enantiomer and its S-enantiomer administrable to a human for lessening the incidence of incontinence.

Another object of this invention is to provide a novel composition that makes available controlled and sustained oxybutynin therapeutic activity to a patient in need of oxybutynin therapy.

Another object of the invention is to provide a novel dosage form manufactured as an osmotic device that can administer oxybutynin to a biological receptor to produce the desired oxybutynin effects.

Another object of the present invention is to provide a dosage form manufactured as an osmotic dosage form that maintains oxybutynin and oxybutynin therapeutically acceptable salts in the dosage form and provide protection from light until the oxybutynin is released from the dosage form, thereby substantially reducing and/or substantially eliminating the unwanted influences of the gastrointestinal environment of use and still provide controlled administration of oxybutynin over time.

Another object of the present invention is to provide a dosage form that administers oxybutynin at a controlled rate over time for its therapeutic benefit accompanied by a lessening of possible unwanted side-effects.

Another object of the present invention is to provide a dosage form that contains initially crystalline oxybutynin salt protected by a light-resistant semipermeable polymeric wall from light and can be administered in a rate-controlled dose over time.

Another object of the present invention is to provide a dosage form adapted for the oral administration of α-cyclohexyl-α-hydroxy-benzeneacetic acid 4-(diethylamino)-2-butynyl ester salt in a first composition in contacting layered arrangement with a second force generating second composition that operates in combination for the controlled administration of the beneficial ester salt.

Another object of the present invention is to provide a complete pharmaceutical oxybutynin regimen comprising a composition comprising oxybutynin that can be dispensed from a drug delivery dosage form, the use of which requires intervention only for initiation and possibly for termination of the regimen.

Another object of the invention is to provide a method for treating incontinence by orally administering oxybutynin from a delivery device in a rate-controlled amount per unit time to a warm-blooded animal in need of incontinence therapy.

Other objects, features and advantages of this invention will be more apparent to those versed in the delivery arts from following detailed specification, taken in conjunction with the accompanying claims.

DETAILED DISCLOSURE OF SPECIFICATION

In one aspect, the present invention provides a therapeutic composition comprising 1 ng to 450 mg (nanogram to milligrams) of oxybutynin, or an oxybutynin therapeutically acceptable salt selected from the group consisting of acetate, bitartrate, citrate, edetate, edisylate, estolate, esylate, fumarate, gluceptate, gluconate, glutamate, hydrobromide, hydrochloride, lactate, malate, maleate, mandelate, mesylate, methylnitrate, mucate, napsylate, nitrate, pamoate, pantothenate, phosphate, salicylate, stearate, succinate, sulfate, tannate and tartrate. The oxybutynin can be present as the racemate, as the R-enantiomer or as the S-enantiomer. The therapeutic composition further contains 40 mg to 250 mg of a polyalkylene oxide selected from the group consisting of a polyethylene oxide of 200,000 molecular weight, or a polyethylene oxide of 300,000 molecular weight, 1 mg to 25 mg of a hydroxypropylalkylcellulose of 9,000 to 150,000 selected from the group consisting of hydroxypropylmethylcellulose, hydroxypropylethylcellulose, hydroxypropylbutylcellulose, and hydroxypropylpentylcellulose, 1 mg to 40 mg of an osmotic solute selected from the osmotically effective compounds consisting of sodium chloride, potassium chloride, potassium acid phosphate, tartaric acid, citric acid, raffinose, magnesium sulfate, magnesium chloride, urea, inositol, sucrose, glucose and sorbital, and 0.01 mg to 5 mg of a lubricant such as calcium stearate, magnesium stearate, magnesium oleate, calcium palmitate, sodium suberate, potassium laureate, salts of fatty acids, salts of alicyclic acids, salts of aromatic acids, stearic acid, oleic acid, palmitic acid, and a mixture of salt of fatty, alicyclic or aromatic acid and a fatty, alicyclic or aromatic acid.

The invention provides for the therapeutic composition comprising the oxybutynin to be administered as the composition neat for increasing the urinary bladder capacity, for diminishing the frequency of uninhibited contractions of the detrusor muscles, and its accompanying delay of the desire to void. The invention provides also the therapeutic composition as a therapeutic layer in layered arrangement with a hydrogel layer that supports the therapeutic layer to yield a bi-layered matrix. The hydrogel layer comprises 40 mg to 250 mg of a polyalkylene oxide of 3,000,000 to 8,000,000 molecular weight selected from the group consisting of polyethylene oxide and polypropylene oxide, or 40 mg to 250 mg of an alkali carboxymethylcellulose of 10,000 to 6,000,000 molecular weight such as sodium carboxymethylcellulose or potassium carboxymethylcellulose, 1 mg to 50 mg of an osmagent selected from the group consisting of sodium chloride, potassium chloride, potassium acid phosphate, tartaric acid, citric acid, raffinose, magnesium sulfate, magnesium chloride, urea, inositol, sucrose, glucose and sorbitol, 0 mg to 5 mg of ferric oxide, 0.1 mg to 30 mg of a hydroxyalkylcellulose of 7,500 to 175,000 molecular weight, or 0.1 mg to 30 mg of a hydroxypropylalkylcellulose of 9,000 to 225,000 molecular weight selected from the group consisting of hydroxyethylcellulose, hydroxypropylmethylcellulose, hydroxypropylcellulose, and hydroxypropylethylcellulose, 0.00 to 1.5 mg of an antioxidant selected from the group consisting of ascorbic acid, butylated hydroxyanisole, butylatedhydroxyquinone, butylhydroxyanisol, hydroxycomarin, butylated hydroxytoluene, cephaim, ethyl gallate, propyl gallate, octyl gallate, lauryl gallate, propylhydroxybenzoate, trihydroxybutylrophenone, dimethylphenol, diterlbulylphenol, vitamin E, lecithin and ethanolamine, and 0.2 mg to 7 mg of a lubricant selected from the group consisting of calcium stearate, magnesium stearate, magnesium oleate, calcium palmitate, sodium suberate, potassium laureate, salts of fatty acids, salts of alicyclic acids, salts of aromatic acids, stearic acid, oleic acid, palmitic acid, a mixture of a salt of a fatty, alicyclic or aromatic acid, and a fatty, alicylic or aromatic acid.

The invention further provides a delivery device for the delivery of the therapeutic composition comprising oxybutynin. The delivery device comprises a wall, which wall surrounds an internal compartment. The wall is semipermeable, as it is permeable to the passage of fluid and impermeable to the passage of oxybutynin. The wall is nontoxic and it comprises a polymer selected from the group consisting of a cellulose acylate, cellulose diacylate, cellulose triacylate, cellulose acetate, cellulose diacetate and cellulose triacetate. The wall comprises 75 weight percent, (wt %) to 100 wt % of the cellulosic wall-forming polymer, or the wall can comprise 0.01 wt % to 10 wt % of polyethylene glycol, or 1 wt % to 25 wt % of a cellulose either selected from the group consisting of hydroxypropylcellulose and hydroxypropylmethylcellulose. The total weight percent of all components comprising wall 12 is equal to 100 wt %. The internal compartment comprises the therapeutic oxybutynin composition in layered position with the expandable hydrogel composition. The expandable hydrogel composition in the compartment increases in dimension and thereby occupies space in the compartment. The therapeutic layer and the expandable layer act together during the operation of the delivery device for the controlled release of oxybutynin to a patient over time. The delivery device comprises a passageway in the wall that connects the exterior of the delivery device with the internal compartment. The delivery device provided by the invention delivers oxybutynin from the device to the patient at a substantially zero order rate of release over a period of twenty-four hours.

The expression passageway, comprises means and methods suitable for the metered release of the therapeutic drug 18 from compartment 15 of dosage form 10. The exit means 13 comprises at least one passageway, orifice, bore, aperture, pore, porous element, hollow fiber, capillary tube, porous overlay, and porous element that provides for the osmotic controlled release of oxybutynin. The expression passageway includes a material that erodes or is leached from the wall in a fluid environment of use to produce at least one dimensioned passageway. Representative materials suitable for forming a passageway, or a multiplicity of passageways comprise a leachable poly(glycolic) acid or poly(lactic) acid polymer in the wall, a gelatinous filament, poly(vinyl alcohol), leachable polysaccharides, salts and oxides. A pore passageway, or more than one pore passageways can be formed by leaching a leachable compound, such as sorbitol, from the wall. The passageway possessing controlled release dimensions such as round, triangular, square, elliptical, and the like, for the metered release of oxybutynin from the delivery device. The delivery device can be constructed with one or more passageways in spaced apart relationship on a single surface or on more than one surface of the wall. Passageways and equipments for forming passageways are disclosed in U.S. Pat. Nos. 3,845,770; 3,916,899; 4,063,064; 4,088,864 and 4,816,263. Passageways formed by leaching are disclosed in U.S. Pat. Nos. 4,200,098 and 4,285,987.

DESCRIPTION OF PROCESSES FOR MANUFACTURING THE DOSAGE FORM OF THE INVENTION

The wall of the delivery device can be formed in one technique using the air suspension procedure. This procedure consists in suspending and tumbling the compressed layers in a current of air and wall-forming composition until a wall is applied to the oxybutynin forming compartment. The air suspensions procedure is well-suited for independently forming the wall. The air suspension procedure is described in U.S. Pat. No. 2,799,241; *J. Am. Pharm. Assoc.*, Vol. 48, pages 451 to 459, 1959; and ibid. Vol. 49, pages 82 to 84, 1960. The wall can also be formed with a wall-forming composition in a Wurster® air suspension coater, using acetone-water co-solvent, 90:10, wt:wt, using 2.5 to 7 wt % polymer solids. The Aeromatic® air suspension coater using a methylene dichloride methanol co-solvent, 87:13, v:v, also can be used for applying the wall. Other wall forming techniques, such as pan coating, can be used for providing the delivery device. In the pan coating system, wall forming compositions are deposited by successive spraying of the composition on the bi-layered compartment, accompanying by tumbling in a rotating pan. A larger volume of co-solvent can be used to reduce the concentration of polymer solids to produce a thinner wall. Finally, the wall coated compartments are laser or mechanically drilled, and then dried in a forced air or humidity oven for 3 days to a week to free the solvent. Generally, the walls formed by these techniques have a thickness of 2 to 20 mils (0.051 to 0.51 mm) with a presently preferred thickness of 2 to 6 mils (0.051 to 0.15 mm).

The delivery device of the invention is manufactured by standard manufacturing techniques. For example, in one manufacture, the beneficial oxybutynin and other ingredients comprising the first layer facing the exit means are blended and pressed into a solid layer. The oxybutynin and other ingredients can be blended also with a solvent and into a solid or semisolid formed by conventional methods such as ball-milling, calendering, stirring or rollmilling and then pressed into a preselected shape. The layer possesses dimensions that correspond to the internal dimensions of the area the layer is to occupy in the delivery device and it also possesses dimensions corresponding to the second layer for forming a contacting arrangement therewith. Next, the oxybutynin hydrogel layer is placed in contact with the oxybutynin layer. The layering of the oxybutynin layer and the hydrogel layer can be fabricated by conventional press-layering techniques. Finally, the two layer compartment forming members are surrounded and coated with an outer wall. A passageway is laser drilled through the wall to contact the oxybutynin layer, with the delivery device optically oriented automatically by the laser equipment for forming the passageway on the preselected surface.

In another manufacture, the delivery device is manufactured by the wet granulation technique. In the wet granulation technique, the oxybutynin and the ingredients comprising the fist layer are blended using an organic or inorganic solvent, such as isopropyl alcohol-methylene dichloride 80/20 v/v as the granulation fluid. Other granulating fluid, such as water or denatured alcohol 100%, can be used for this purpose. The ingredients forming the first layer are individually passed through a 40 mesh screen and then thoroughly blended in a mixer. Next, other ingredients comprising the first layer are dissolved in a portion of the granulation fluid, such as the co-solvent described above. Then, the latter prepared wet blend is slowly added to the oxybutynin blend with continual mixing in the blender. The granulating fluid is added until a wet blend is produced, which wet mass then is forced through a 20 mesh screen onto oven trays. The blend is dried for 18 to 24 hours at 25° C. to 40° C. The dry granules are screened then with a 16 mesh screen. Next, a lubricant is passed through an 60 mesh screen and added to the dry screened granule blend. The granulation is put into milling jars and mixed on a jar mill for 2 to 10 minutes. The first and second layer compositions are pressed into a layered tablet, for example, in a Manesty® layer press.

Another manufacturing process that can be used for providing the oxybutynin and hydrogel composition comprises blending their powdered ingredients in a fluid bed granulator. After the powdered ingredients are dry blended in the granulator, a granulating fluid, for example poly (vinylpyrrolidone) in water, is sprayed onto the respective powders. The coated powders are then dried in a granulator. This process coats-agglomerates all the ingredients present therein while spraying the granulating fluid. After the granules are dried, a lubricant such as stearic acid or magnesium stearate is blended as above into the mixture. The granules are pressed then in the manner described above. In an embodiment, when the fluid bed granulating process is used to manufacture the hydrogel layer, the antioxidant is initially present in the polyalkylene oxide by the manufacturer, it is removed during processing. Thus, if an antioxidant is desired, it becomes necessary to add additional antioxidant to the hydrogel formulation, and this addition can be accomplished during the fluid bed granulation described above.

The device of this invention is manufactured in another embodiment by mixing the oxybutynin with composition forming ingredients and pressing the composition into a solid layer possessing dimensions that correspond to the internal dimensions of the compartment space adjacent to a passageway. In another embodiment, the oxybutynin and other first composition forming ingredients and a solvent are mixed into a solid, or semi-solid, by conventional methods such as ballmilling, calendering, stirring or rollmilling, and then pressed into a preselected layer forming shape.

In the manufactures as presented above, the manufacture comprising a layer of a composition comprising an osmopolymer hydrogel and an optional osmagent are placed in contact with the layer comprising the drug oxybutynin and the two layers comprising the layers are surrounded with a semipermeable wall. The layering of the first drug oxybutynin composition and the second osmopolymer hydrogel and optional osmagent composition can be accomplished by using a conventional two-layer tablet press technique. The wall can be applied by molding, spraying or dipping the pressed shapes into wall forming materials. Another and presently preferred technique that can be used for applying the wall is the air suspension coating procedure. This procedure consists in suspending and tumbling the two layers in a current of air until the wall forming composition surrounds the layers. Manufacturing procedures are described in *Modern Plastics Encyclopedia*, Vol. 46, pp 62–70 (1969); and in *Pharmaceutical Science*, by Remington, 14th Ed., pp 1626–1979, (1970), published by Mack Publishing Co., Easton, Pa. The delivery device can be manufactured by following the teaching in U.S. Pat. Nos. 4,327,725, 4,612,008; 4,783,337; 4,863,456; and 4,902,514.

Exemplary solvents suitable for manufacturing the wall, the laminates and laminae include inert inorganic and organic solvents that do not adversely harm the materials and the final wall of the final laminated wall. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptaene, ethylene glycol monoethyl ether, ethylene glycol monoethylacetate, methylene dichloride, ethylene dichloride, propylene dichloride, carbon chloroform, nitroethane, nitropropane, tetrachloroethane, ethyl ether, isopropyl ether, cyclohexane, cycl-octane, toluene, naphtha, 1,4-dioxane, tetrahydrofuran, diglyme, aqueous and non-aqueous mixtures thereof, such as acetone and water, acetone and methanol, acetone and ethyl alcohol, methylene dichloride and methanol, and ethylene dichloride and methanol.

DETAILED DISCLOSURE OF EXAMPLES PROVIDED BY THE INVENTION

The following examples are merely illustrative of the present invention and they should not be considered as limiting the scope of the invention in any way as these examples and other equivalents thereof will become apparent to those versed in the art in the light of the present disclosure, the drawings and the accompanying claims.

EXAMPLE 1

The therapeutic oxybutynin composition provided by the invention was prepared as follows: first, 103 grams of oxybutynin hydrochloride was dissolved in 1200 millimeters of anhydrous ethanol. Separately, 2,280 g of polyethylene oxide of 200,000 molecular weight, 150 g of hydroxypropylmethylcellulose of 9,200 molecular weight and 450 g of sodium chloride were dry blended in a conventional blender for 10 minutes to yield a homogenous blend. Next, the oxybutynin ethanol solution was added slowly, with the mixer continuously blending until all the solution was added to the three component dry blend, with the mixing continued for another 8 to 10 minutes. The blended wet composition was passed through a 16 mesh screen and dried over night at a room temperature of 72° F. (22.2°). Then, the dry granules were passed through a 20 mesh screen and 18 g of magnesium stearate were added and all the ingredients blended again for 5 minutes. The fresh granules are ready for formulation into a therapeutic oxybutynin composition. The therapeutic composition comprises 3.4 wt % oxybutynin hydrochloride, 76 wt % polyethylene oxide of 200,000 molecular weight, 5 wt % of hydroxypropylmethylcellulose of 9,200 molecular weight, 15 wt % sodium chloride, and 0.6 wt % mageseum stearate. The therapeutic composition can be administered as the composition for its intended therapy.

EXAMPLE 2

The osmopolymer, hydrogel composition provided by the invention was prepared as follows: first 1274 g of pharmaceutically acceptable polyethylene oxide comprising a 7,500,000 molecular weight, 600 g of sodium chloride, and 20 g ferric oxide were separately screened through a 40 mesh screen. Then, all the screened ingredients were mixed with 100 g of hydroxypropylmethylcellulose of 11,200 molecular weight to produce a homogenous blend. Next, 300 ml of denatured anhydrous alcohol was added slowly to the blend with continuous mixing for 5 minutes. Then, 1.6 g of butylated hydroxytoluene was added followed by more blending with 5 g of magnesium stearate added with 5 minutes of blending to yield a homogenous blend. The freshly prepared granulation is passed through a 20 mesh screen and allowed to dry for 20 hours at 22.2° C. The final composition comprised 63.67 wt % of the polyethylene oxide, 30 wt % of sodium chloride, 1 wt % of ferric oxide, 5 mg of hydroxypropylmethylcellulose, 0.08 wt % of butylated hydroxytoluene, and 0.25 mg of magnesium stearate.

EXAMPLE 3

The osmopolymer, hydrogel composition provided by the invention was prepared as follows: first 1274 g of pharmaceutically acceptable sodium carboxymethylcellulose comprising a 5,250,000 molecular weight, 600 g of sodium chloride, and 20 g ferric oxide were separately screened through a 40 mesh screen. Then, all the screened ingredients were mixed with 100 g of hydroxypropylmethylcellulose of 11,200 molecular weight, and 100 g of hydroxypropylcellulose of 30,000 molecular weight to produce a homogenous blend. Next, 300 ml of denatured anhydrous alcohol was added slowly to the blend with continuous mixing for 5 minutes. Then, 1.6 g of butylated hydroxytoluene was added followed by more blending with 5 g of magnesium stearate added with 5 minutes of blending to yield a homogenous blend. The freshly prepared granulation is passed through a 20 mesh screen and allowed to dry for 20 hours at 22.2° C. The final composition comprised 58.67 wt % of the sodium carboxymethylcellulose, 30 wt % of sodium chloride, 1 wt % of ferric oxide, 5 mg of hydroxypropylmethylcellulose, 5 mg of hydroxypropylcellulose, 0.08 wt % of butylated hydroxytoluene, and 0.25 mg of magnesium stearate.

EXAMPLE 4

The therapeutic oxybutynin composition and the osmopolymer hydrogel composition were made into a bilayer tablet as follows: first, 147 mg of the oxybutynin composition was added to a punch die set, and tamped, then, 98 mg of the hydrogel composition was added and the two layers compressed under a pressure head of 1.0 ton (1000 kg) into a 11/32 inch (0.873 cm) diameter, contacting intimate bilayered tablet.

EXAMPLE 5

The bilayered tablet was manufactured into a delivery device as follows: first, a semipermeable wall-forming composition was prepared comprising 95 wt % cellulose acetate having a 39.8% acetyl content and 5 wt % polyethylene glycol having a molecular weight of 3350 by dissolving the ingredients in a co-solvent comprising acetone and water in 90:10 wt:wt composition to make a 4% solid solution. The wall-forming composition was sprayed onto and around the bilayered core to provide a 26.4 mg semipermeable wall.

Next, the semipermeable walled bilayered tablet was laser drilled through the semipermeable wall to provide a 20 mil (0.51 mm) to contact the oxybutynin layer with the exterior of the delivery device. The residual solvent was removed by drying for 48 hours at 50° C. and 50% relative humidity. Next the delivery devices were dried further for 1 hour at 50° C. to remove excess moisture. The delivery device provided by this manufacture provides 3.4 wt % oxybutynin hydrochloride, 76 wt % polyethylene oxide of 200,000 molecular weight, 5 wt % hydroxypropylmethylcellulose of 9,200 molecular weight, 0.6 wt % magnesium stearate, and 15 wt % sodium chloride in the therapeutic oxybutynin composition. The osmopolymer, hydrogel push composition comprises 63.67 wt % polyethylene oxide of 7,500,000 molecular weight, 30 wt % sodium chloride, 1 wt % ferric chloride, 5 wt % hydroxypropylmethylecellulose of 9,200 molecular weight, 0.08 wt % butylated hydroxytoluene, and 0.25 wt % magnesium stearate. The semipermeable wall comprises 95 wt % cellulose acetate comprising 39.8% acetyl content, and 5 wt % polyethylene glycol of 3350 molecular weight. The delivery device comprises an exit passage of 20 mils (0.50 mm) and it has a mean release rate of 0.260 mg/hr for 23.8 hours. The semipermeable wall provides substantial protection from photo (light) degradation of the oxybutynin in the delivery device.

EXAMPLE 6

A dosage form, prepared according to the above, comprising a drug layer consisting of 6.67 wt % oxybutynin hydrochloride, 87.83 wt % polyethylene oxide of 200,000 molecular weight, 5.00 wt % hydroxypropylmethylcelulose, and 0.50 wt % magnesium stearate; in layered contact with a push layer comprising 58.75 wt % sodium carboxymethylcellulose, 30 wt % sodium chloride 5.00 wt % hydroxypropylmethylcellulose, 1.00 wt % ferric oxide, 5.00 wt % hydroxypropylcellulose and 0.25 wt % magnesium stearate; which bilayered core is surrounded by a semipermeable wall comprising cellulose acetate and polyethylene glycol; and an exit pod through the wall for delivering the oxybutynin at a controlledrate over thirty hours.

EXAMPLE 7

The dosage form acording to claim 6 wherein hydroxypropylmethylcellulose is a member selected from the group consisting of 9,200 and 11,200 molecular weight; the polyethylene oxide has a 300,000 molecular weight; the sodium carboxymethylcellulose is a member selected from the group consisting of 700,000 or 800,000 or 900,000 or 1,000,000 molecular weight; the hydroxypropylcellulose is a member selected from the group consisting of 25,000 or 30,000 or 40,000 molecular weight; and the dosage form comprises 5 mg to 250 mg of oxybutynin pharmaceutically acceptable salt.

DISCLOSURE OF USE OF THE DOSAGE FORM FOR PERFORMING A METHOD OF PRACTICING THE INVENTION

The invention pertains additionally to the use of the delivery device by providing a method for delivering oxybutynin at a controlled rate orally to a warm-blooded animal in need of oxybutynin therapy, wherein the use comprises the steps of: (A) admitting into the warm-blooded animal a delivery device expressing a dosage form comprising: (1) a wall surrounding a compartment, the wall comprising a semipermeable polymeric composition permeable to the passage of fluid and substantially impermeable to the passage of oxybutynin; (2) an oxybutynin layer in the compartment comprising oxybutynin; (3) a hydrogel push layer in the compartment comprising an osmotic formulation for imbibing and absorbing fluid for expanding in size for pushing the oxybutynin composition from the delivery device; (4) at least one passageway in the wall for releasing the oxybutynin; (B) imbibing fluid through the semipermeable wall at a fluid-imbibing rate determined by the permeability of the semipermeable wall and the osmotic pressure across the semipermeable wall causing the push layer to expand; and (C) delivering the therapeutically active oxybutynin from the delivery device through the exit passageway to a warm-blooded animal over a prolonged period of time up to 24 hours. The oxybutynin is administered by the method of the invention for antispasmodic therapy. The oxybutynin is administered to patients with uninhibited neurogenic and reflex neurogenic bladder for increased vesual capacity which diminishes the frequency of uninhibited contractions of the detrusor muscle and delays the desire to void. The dosage form is indicated for the relief of symptoms associated with voiding such as urgency, urge incontinence, frequency, nocturia and incontinence in patients in neurogenic bladder.

The dosage form of this invention, as seen from the above disclosure can be used in a method for administering a drug by the oral route, and in another method, the dosage form can be sized and shaped for administering a drug by the sublingual and buccal routes. The sublingual and buccal routes can be used for quicker therapy and they can be used when a smaller dose of drug is needed for immediate therapy. The latter routes can be used as a by-pass of the first pass of hepatic metabolism of the drug.

In summary, it will be appreciated that the present invention contributes to the art an unobvious dosage form that possesses practical utility, can administer a drug at a dose metered release rate per unit time. While the invention has been described and pointed out in detail with reference to operative embodiments thereof, it will be understood by those skilled in the art that various changes, modifications, substitutions and omissions can be made without departing from the spirit of the invention. It is intended, therefore, that the invention embraces those equivalents within the scope of the claims which follow.

We claim:

1. A therapeutic composition comprising: 1 ng to 450 mg of oxybutynin, 40 mg to 250 mg of polyalkylene oxide, 1 mg to 25 mg of hydroxypropylalkylcellulose, and 0.01 mg to 5 mg of a lubricant.

2. The therapeutic composition according to claim 1, wherein the oxybutynin is a therapeutically acceptable salt selected from the group consisting of acetate, bitartrate, citrate, edetate, edisylate, estolate, esylate, fumarate, gluceptate, gluconate, glutamate, hydrobromide, hydrochloride, lactate, malate, maleate, mandelate, mesylate, methylnitrate, mucate, napsylate, nitrate, pamoate, pantothenate, phosphate, salicylate, stearate, succinate, sulfate, tannate, and tartrate.

3. A bilayered tablet comprising a therapeutic layer comprising 1 ng to 450 mg of oxybutynin, 40 mg to 450 mg of polyalkylene oxide, 1 mg to 25 mg of hydroxypropylalkylcellulose and 0.01 mg to 5 mg of a lubricant; in contact with a hydrogel layer comprising 40 mg to 250 mg of polyalkylene oxide, 10 mg to 50 mg of an osmagent, 0.1 mg to 20 mg of hydroxypropylalkylcellulose, 0.0 ng to 1.5 mg of an antioxidant, and 0.2 mg to 7 mg of a lubricant.

4. A bilayered tablet comprising a therapeutic layer comprising a therapeutic layer comprising 1 ng to 450 mg of oxybutynin, 40 mg to 250 mg of polyalkylene oxide, 1 mg to 25 mg of hydroxypropylalkylcellulose, and 0.01 mg to 5 mg of a lubricant; said layer in contact with a push layer comprising 40 mg to 250 mg of an alkali carboxymethylcellulose, 10 mg to 50 mg of an osmagent, 0.1 mg to 20 mg of hydroxypropylalkylcellulose, 0.1 mg to 30 mg of hydroxyalkylcellulose, 0.0 ng to 1.5 mg of an antioxidant, and 0.2 mg to 7 mg of a lubricant.

5. A delivery device for administering oxybutynin to a patient in need of oxybutynin, wherein the delivery device comprises: a layer comprising 1 ng to 450 mg of oxybutynin, 40 mg to 250 mg of polyalkylene oxide, 1 mg to 25 mg of hydroxypropylalkylcellulose, and 1 mg to 50 mg of an osmagent; and contacting layer comprising 40 mg to 250 mg of an osmopolymer and 10 mg to 50 mg of an osmagent; a semipermeable wall that surrounds the layers, which semipermeable wall is permeable to the passage of fluid, and impermeable to the passage of oxybutynin, and an exit through the semipermeable wall for administering the oxybutynin to the patient at a controlled rate over time.

6. A delivery device for administering oxybutynin to a patient in need of oxybutynin, wherein the delivery device comprises: a drug layer comprising 1 ng to 450 mg of oxybutynin, 40 mg to 250 mg of polyalkylene oxide, 1 mg to 25 mg of hydroxypropylalkylcellulose, 1 mg to 50 mg of an osmagent; and a contacting displacement layer comprising 40 mg to 250 mg of carboxymethylcellulose and 10 mg to 50 mg of an osmagent; a semipermeable wall that surrounds the layers, which semipermeable wall is permeable to the passage of fluid, and impermeable to the passage of oxybutynin, and an exit through the semipermeable wall for administering the oxybutynin to the patient at a controlled rate over time.

7. A delivery device for administering oxybutynin to a patient in need of oxybutynin, wherein the delivery device comprises: a drug layer comprising 1 ng to 450 mg of oxybutynin, 40 mg to 250 mg of polyalkylene oxide, 1 mg to 25 mg of a hydroxypropylalkylcellulose, 1 mg to 50 mg of an osmagent; and a contracting displacement layer comprising 40 mg to 250 mg of polyalkylene oxide, and 10 mg to 50 mg of an osmagent; a semipermeable wall that surrounds the layer, which semipermeable wall is permeable to the passage of fluid, and impermeable to the passage of oxybutynin, and an exit through the semipermeable wall for administering the oxybutynin to the patient at a controlled rate over time.

* * * * *